United States Patent [19]

Christensen et al.

[11] 4,007,196
[45] * Feb. 8, 1977

[54] 4-PHENYLPIPERIDINE COMPOUNDS

[75] Inventors: Jørgen Anders Christensen, Virum; Richard Felt Squires, Gl. Olstykke, both of Denmark

[73] Assignee: A/S Ferrosan, Denmark

[ * ] Notice: The portion of the term of this patent subsequent to Oct. 14, 1992, has been disclaimed.

[22] Filed: July 23, 1975

[21] Appl. No.: 598,146

Related U.S. Application Data

[63] Continuation-in-part of Ser. No. 435,006, Jan. 21, 1974, Pat. No. 3,912,743.

[30] Foreign Application Priority Data

Jan. 30, 1973  United Kingdom ............... 4496/73

[52] U.S. Cl. .......................... 260/293.58; 424/267
[51] Int. Cl.² ....................................... C07D 405/12
[58] Field of Search .............................. 260/293.58

[56] References Cited

UNITED STATES PATENTS 2,976,291  3/1961  Jacob et al. .................... 260/294.7
3,178,438  4/1965  Clarke ........................... 260/294.7

*Primary Examiner*—G. Thomas Todd
*Attorney, Agent, or Firm*—Wenderoth, Lind & Ponack

[57] ABSTRACT

The invention relates to new 3-substituted 1-alkyl-4-phenylpiperidines, being useful as antidepressant and anti-Parkinson agents, and to their production.

4 Claims, No Drawings

4-PHENYLPIPERIDINE COMPOUNDS

This application is a continuation-in-part of our patent application, Ser. No. 435,006, filed January 21, 1974, now U.S. Pat. No. 3,912,743, relating to novel 3-substituted 1-alkyl-4-phenylpiperidines having interesting pharmacological properties which make them useful as antidepressants and anti-Parkinson agnets.

The present invention relates to a group of 3-substituted 1-alkyl-4-phenylpiperidines not specifically disclosed in the parent application, and not only having the said properties to a degree far exceeding those of the previously disclosed compounds, but also having a greatly protracted effect as compared with the previously disclosed compounds.

More particularly, the invention relates to a 3-substituted 1-alkyl-4-phenylpiperidine of the formula

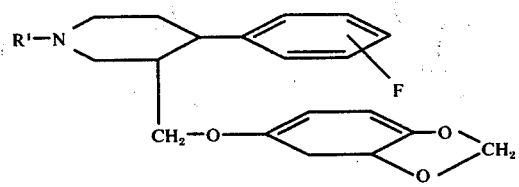
(I)

wherein $R^1$ represents hydrogen or an alkyl group of 1–4 carbon atoms, and the fluorine atom may be in any of the available positions, and a salt thereof with a pharmaceutically acceptable acid.

Of particularly therapeutical effect is the (−) form of a compound of formula I, wherein $R^1$ is hydrogen and the fluorine is in para position.

Examples of the alkyl groups represented by $R^1$ are the methyl, ethyl, propyl, isopropyl, n-butyl, and tert-butyl groups. Of these, the compound where $R^1$ is methyl is preferred.

The salt forming acids may be any of the available, pharmaceutically acceptable acids, whether inorganic or organic.

The compounds of formula I are prepared from the corresponding carbinols which can be prepared by reducing a compound of the formula II wherein $R^1$ is as hereinbefore defined, preferably with a complex metal hydride reducing agent, especially lithium aluminium hydride.

Compounds having the formula II may be prepared as described by J. T. Plati, A. K. Ingberman and W. Wenner (J. Org. Chem. 1957: 22, 201) who prepare the compound in which the fluorine is replaced by hydrogen, and $R^1$ is methyl by treating arecoline (methyl-1,2,5,6-tetrahydro-3-pyridine-carboxylate) with phenyl magnesium bromide.

In the same manner, other compounds used as starting material for the desired piperidine carbinols are prepared using the appropriate arecoline homologue and F-phenyl magnesium bromide. The reaction gives the two isomers, the cis form ($\alpha$) and the trans form ($\beta$) (carbon atoms 3 and 4 in the piperidine ring). Both forms can again be resulved into a (+) and a (−) form.

The compounds of the invention may be prepared from the piperidine carbinols using different processes as illustrated in the following reaction schemes, wherein $R^1$ is as herein-before defined, X represents fluorine, and R is the group

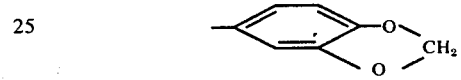

Method A

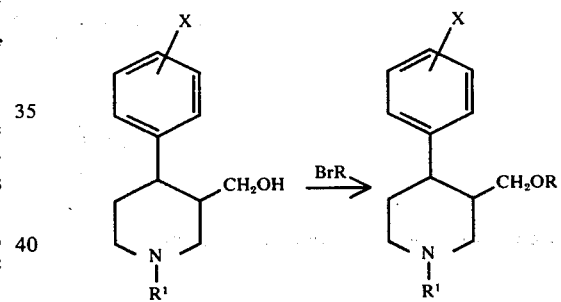

The alkali metal compound of the piperidine carbinol is treated with an active ester corresponding to the desired R substituent.

Method B

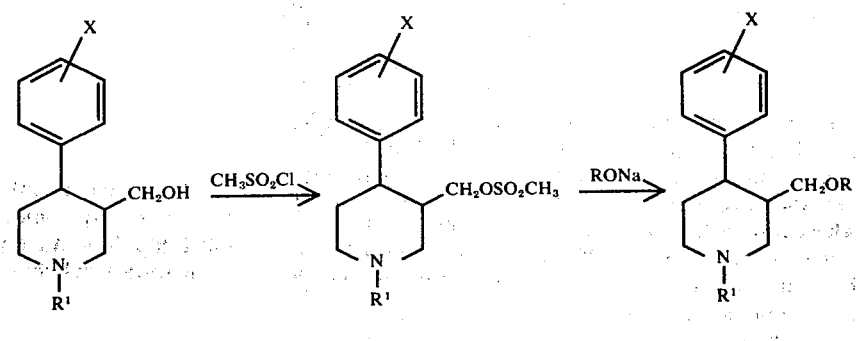

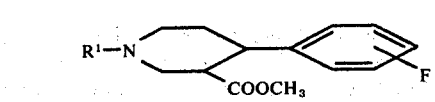
(II)

The piperidine carbinol is converted into an ester, e.g. the methane sulfonic ester, using methane sulfochloride in pyridine, and reacting with RONa, R being as above.

Using method A, the α-form of the carbinol gives the α-form of the ether, whereas the β-form of the carbinol gives the β-form of the ether.

Using method B, the α-form of the carbinol gives the α-form of the ether, but surprisingly the β-form of the carbinol gives a mixture of the α-form and the β-form, mainly the α-form.

Method C

Two hydroxy compounds are condensed using dicyclohexylcarbodiimide as a condensing agent;

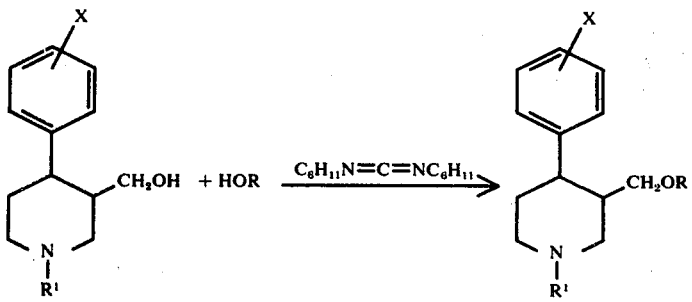

In this method the α-carbinols give α-ethers, and the β-carbinols give a mixture of α- and β-ethers.

According to another method the compounds of the invention are prepared from compounds of formula I, wherein $R^1$ is hydrogen or an acyl group.

If $R^1$ is hydrogen, the compound is alkylated, and if $R^1$ is an acyl group, the group is reduced to give the corresponding alkyl group, or the acyl group is removed by hydrolyzing to leave the NH group which is then alkylated.

Usually one of the optical active forms of the new compounds is therapeutically more active than the other. To isolate this form the resolution may be accomplished as the final step, or the resolution may be accomplished at an earlier stage, before the carbinol group of the piperidine is converted to an ether group.

Thus, for instance, the racemic form of the compound of formula II, in which $R^1$ is methyl, and the fluorine is in para position may be converted into the α-form by treatment with sodium methoxide, a racemic mixture of (−) menthol esters being prepared from said α-form and resolved into the (−) menthol esters of α(+) and α(−)-1-methyl-4-phenylnipecotinic acid as illustrated by the following scheme of reaction

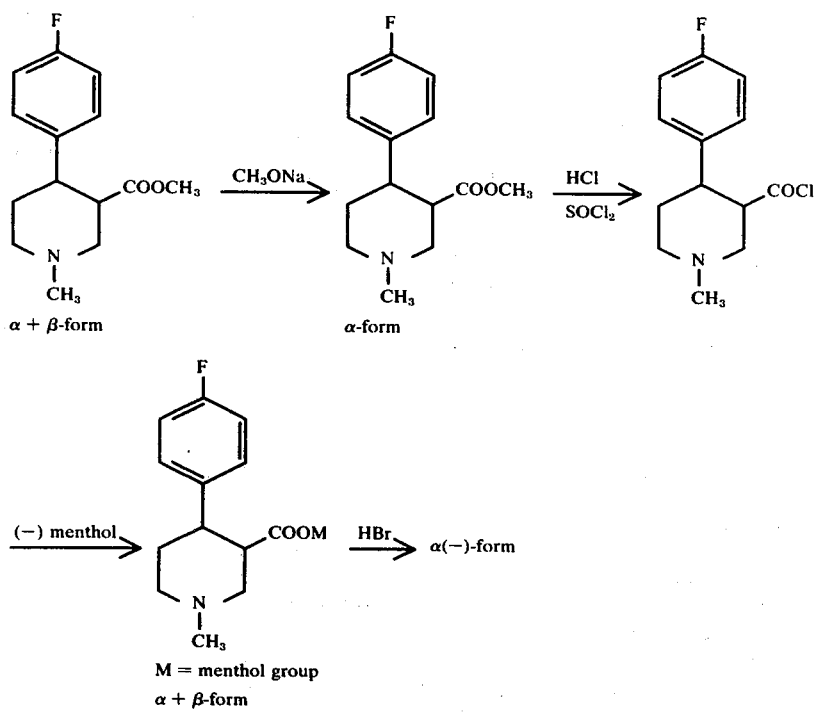

The two esters can then be reduced individually with LiAlH$_4$ to the menthol esters of α(+) and α(−)-3-hydroxy-methyl-1-methyl-4-phenylpiperidine, from which the desired ethers are prepared by reacting with 1,3-benzdioxolyl chloride:

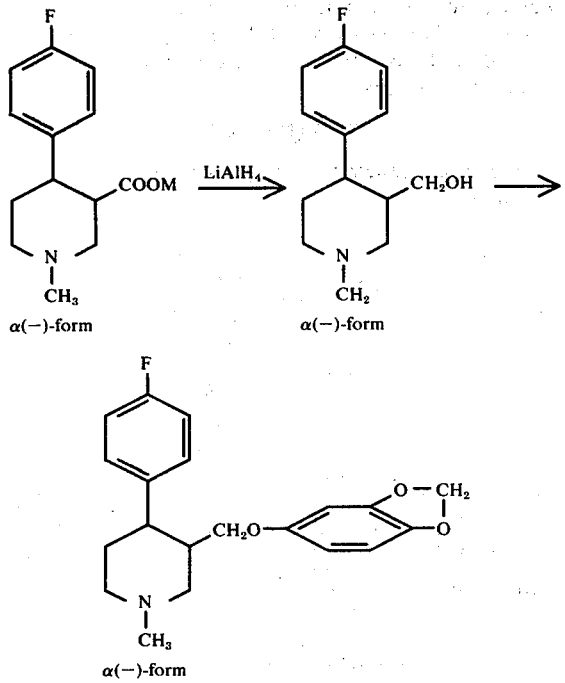

α(−)-form     α(−)-form

α(−)-form

In an alternative method of preparing the optically active carbinol to be converted into an ether of the invention a racemic mixture of a tetrahydropyridine of the formula

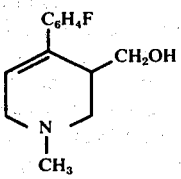

is resolved into the optically active isomers which are then reduced individually before being converted into an ether of the invention.

The following Examples are illustrative of the compounds of the invention and their preparation without being limiting.

EXAMPLE 1

(−)-α-4-(4-Fluorophenyl)-3-(1,3-benzdioxolyl-(3))-oxymethyl-N-methyl-piperidine maleate A. 251 g of methyl-4-(4-fluorophenyl)-N-methyl-nipecotinate (prepared according to J. T. Plati), 8 g of sodium methoxide and 500 ml benzene were refluxed for 2 hours. The benzene solution was washed with cold water and evaporated to give the pure α-ester which was dissolved in a mixture of 320 ml of water and 450 ml concentrated hydrochloric acid. The solution was slowly distilled to remove methanol and finally evaporated to dryness in vacuo.

400 ml thionyl chloride were added in small portions to the solid. The mixture was allowed to stand for 3 hours at room temperature and was then evaporated to dryness in vacuo with tetrachloroethane giving methyl-4-(4-fluorophenyl)-N-methylnipecotic acid chloride. The acid chloride was added in small portions to a solution of 160 g (−)-menthol in 800 ml pyridine at a temperature of 0°–5° C. The mixture was allowed to stand at room temperature to the next day. Icewater and 50% sodium hydroxide were added, and the mixture was extracted with ether. The ether was dried with anhydrous magnesium sulphate, filtered and evaporated. Distillation in vacuo gave the menthol ester in a yield of 75–80%. B.p. at 0.05 mm Hg was 165°–170° C.

B. To a solution of 365 g (1 mole) of the said menthol ester in 1000 ml of 99% ethanol were added 93 g of 48% hydrobromic acid (0.55 mole). The crystals were filtered off with suction and recrystallized from 96% ethanol to yield the pure hydrobromide with m.p. 275°–276° C. From this hydrobromide the base was liberated and reduced with lithium aluminium hydride to give an almost quantitative yield of (−)-α-4-(4-fluorophenyl)-3-hydroxymethylpiperidine.

$[\alpha]_D^{20} = -40°$ (c = 5, ethanol).

C. To a solution of 170 ml thionyl chloride in 600 ml of chloroform was added dropwise a solution of 111.5 g (0.5 mole) of the (−)-α-carbinol of step B in 600 ml of CHCl$_3$, the temperature being kept below 10° C. The mixture was refluxed for 6 hours on a steam bath. Thereafter, the mixture was evaporated in vacuo to dryness and shaken in a separating funnel with a cold 25% potassium carbonate solution and ether. The ether layer was dried with anhydrous magnesium sulphate, evaporated and distilled under reduced pressure. The yield of chloro-compound (b.p. at 0.05 mm Hg = 81°–83° C) was 90–95% (from the carbinol). $[\alpha]_D^{20} = -36°$ (c = 5, ethanol).

To a solution of sodium (4.63 g) in methanol (125 ml) were added 3,4-methylenedioxyphenol (29 g) and the chlorocompound (41 g). The mixture was stirred and refluxed for 16 hours. After removal of the solvent in vacuo, the evaporation residue was poured into a mixture of ice (150 g), water (150 ml), and ether (200 ml). The ether layer was separated, and the aqueous layer was extracted with ether. The combined ether solutions were washed with water and dried with anhydrous magnesium sulphate, and the ether was evaporated. The residue was triturated with 200 ml of 99% ethanol and 11.5 ml of concentrated hydrochloric acid, yielding 15.8 g of (−)-α-4-(4-fluorophenyl)-3-(1,3-benzdioxolyl-(3))-oxymethylpiperidine as the hydrochloride with m.p. 230° C.

EXAMPLE 2

(−)-α-4-(4-Fluorophenyl)-3-(1,3-benzdioxolyl-(3))-oxymethyl piperidine maleate (GF 74)

To a solution of 34.3 g (0.1 mole) of the piperidine derivative of Example 1 in 250 ml of methylene chloride was added dropwise a solution of 18 g phenylchloroformate in 125 ml methylene chloride, the temperature being kept between 0° and 5° C. The mixture was allowed to stand until next day at room temperature. The solution was washed with 250 ml of 1M sodium hydroxide and then with 250 ml of 1M hydrochloric acid. The methylene chloride solution was dried and evaporated to leave a solid mixture.

The mixture was suspended in 300 ml benzene, filtered and evaporated. The evaporation residue was refluxed with 25 g of potassium hydroxide and 150 ml of methylcellosolve for 4 hours, and then evaporated in vacuo. Water was added, and the mixture was extracted with benzene. The benzene solution was dried and evaporated, giving (−)-α-4-fluorophenyl-3-(1,3-benzdioxolyl-(3))-oxymethylpiperidine.

To a solution of the latter in ether was added the equivalent amount of maleic acid in ether. The maleate crystallized and after recrystallization from 99% ethanol-ether the m.p. was 136°–138° C. $[\alpha]_D^{20} = -87°$ ($c = 5$, ethanol).

EXAMPLE 3

Resolution of racemic 4-(4-fluorophenyl)-3-(1,3-benzdioxolyl-(3))-oxymethyl)-1-methylpiperidine (VII)

The racemic base (3.43 g) and (+) tartaric acid was dissolved in 20 ml of water. On cooling the solution, 1.8 g of (−) (VII) (+) tartrate was recovered, having $[\alpha]_D^{20} = -40°$ ($c = 5$). The hydrochloride had $[\alpha]_D^{20} = -80°$ ($c = 5$). M.p. 205°–206° C.

EXAMPLE 4

(−)-α-4-(4-Fluorophenyl)-3-(1,3-benzdioxolyl-(3)-oxymethyl)-1-methylpiperidine, hydrochloride A. Racemic 4-(4-fluorophenyl)-3-hydroxymethyl-1-methyl-1,2,3,6-tetrahydropyridine 4-(4-Fluorophenyl)-1-methyl-1,2,3,6-tetrahydropyridine (50 g) was dissolved in a mixture of 21.6 ml of concentrated sulphuric acid and 50 ml of water. To the solution were added 25 ml of concentrated hydrochloric acid and 22.4 ml of 37% formaldehyde solution. The mixture was refluxed for 5 hours, cooled, and 125 ml of concentrated ammonia were added. The mixture was extracted with 50 ml of toluene. Drying of the toluene solution and distillation gave 38 g of 4-(4-fluorophenyl)-3-hydroxymethyl-1-methyl-1,2,3,6-tetrahydropyridine with b.p. 110°–120° C at 0.1 mm Hg.

B. Resolution of 4-(4-fluorophenyl)-3-hydroxymethyl-1-methyl-1,2,3,6-tetrahydropyridine 13 g of the racemic compound and 22 g of (−)-dibenzoyltartaric acid were dissolved in 105 ml of hot methanol. On cooling, 9 g of salt crystallized. M.p. 167°–168° C. The base had $[\alpha]_D^{20} = -140°$ ($c = 5$).

C. (+)-β-4-(4-Fluorophenyl)-3-hydroxymethyl-1-methyl-piperidine 38 g of (−)-4-(4-fluorophenyl)-3-hydroxymethyl-1-methyl-1,2,3,6-tetrahydropyridine were dissolved in 350 ml of 99% ethanol, 5 g of 5% palladium on carbon were added, and the mixture was treated with hydrogen until 4500 ml were absorbed. The catalyst was filtered off, and the solution was evaporated to yield 37.5 g of (+)-β-4-(4-fluorophenyl)-3-hydroxymethyl-1-methyl-piperidine.

D. (−)-α-4-(4-fluorophenyl)-3-(1,3-benzdioxolyl-(3)-oxymethyl)-1-methylpiperidine Using the method given in Example 1, and starting with 37.5 g of (+)-β-4-(4-fluorophenyl)-3-hydroxymethyl-1-methylpiperidine and 29 g of 3,4-methylenedioxyphenol, 30 g of (−)-β-4-(4-fluorophenyl-3-(1,3-benzdioxolyl-(3)-oxymethyl)-1-methylpiperidine, hydrochloride were obtained. M.p. 202° C. $[\alpha]_D^{20} = -84°$ ($c = 5$).

EXAMPLES 5–9

In similar manner the compounds listed below were prepared:

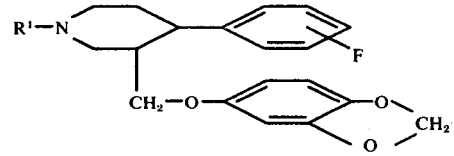

| Code | R¹ | α-Form | Position of fluorine | M.P. °C | Salt |
|------|-----|--------|---------------------|---------|------|
| GF 73 | H | (+) | para | 136.5–137.5 | Maleate |
| GF 75 | CH₃ | (±) | ortho | 217 –218 | HCl |
| GF 76 | CH₃ | (±) | meta | 219 | HCl |
| GF 77 | H | (±) | para | 144 | Maleate |
| GF 78 | H | (±) | meta | 135 | Maleate |

As stated hereinbefore, the compounds of formula I are useful as antidepressants and as anti-Parkinson drugs as indicated by their biochemical and pharmacological properties.

At present the antidepressants most used in the clinic are the tricyclic thymoleptics (e.g. Imipramine and Amitriptyline). These drugs act by centrally potentiating serotonin (5HT) and noradrenaline (NA) as a consequence of neuronal reuptake inhibition.

The same potentiating action of the new compounds was confirmed by determinating 5HT- and Na-uptake inhibition in vitro using synaptosomes prepared from different regions of rat brain.

In the Table below the 5HT-uptake inhibitory activity of the compound GF 74 of the invention is compared with that of some compounds of the parent application and of the above mentioned tricyclic thymoleptics.

Known tricyclic thymoleptics affect the cardiovascular and peripheral autonomic nervous systems causing a wide range of side-effects. Cardiac disturbances and varying degrees of hypotension occur rather frequently and may be very serious. Compounds accordint to the parent application and to this invention, e.g. GF 32 and GF 74, respectively, are more active 5HT potentiators than is Imipramine, but affect the cardiovascular system less than do the most common tricyclic thymoleptics, and therefore lack the more serious side-effects mentioned.

5HT-uptake inhibitory activity

Antagonism of p-chloroamphetamine (PCA)-induced 5HT-depletion from rat brain:

| Substance | 1) ED₅₀ mg/kg s.c. | 2) ED₅₀ mg/kg p.o. | 3) ED₅₀ mg/kg p.o. | 4) ED₅₀ mg/kg p.o. |
|-----------|---------------------|---------------------|---------------------|---------------------|
| GF 32 | 1.5 | 20 | + | |
| GF 61 | 1.4 | | + | |
| GF 52 | 2.8 | 3.2 | + | |
| GF 57 | 0.5 | 2.0 | + | |

-continued

| Substance | 1) ED$_{50}$ mg/kg s.c. | 2) ED$_{50}$ mg/kg p.o. | 3) ED$_{50}$ mg/kg p.o. | 4) ED$_{50}$ mg/kg p.o. |
|---|---|---|---|---|
| GF 74 | 0.2 | | 0.8 | 2–10 |
| Imipramine | 8.0 | 44 | + | |
| Chlorimipramine | 1.0 | 42 | + | |

1) Test drugs were administered s.c. simultaneously with PCA.
2) Test drugs were administered 2 hours before PCA.
3) Test drugs were administered 3 hours before PCA.
4) Test drugs were administered 18 hours before PCA.

It will be noted from the figures given in the Table that the ED$_{50}$-value of the compound of the invention is much smaller than that of any of the comparison compounds, and that whereas none of these showed activity more than two hours after the administration, the compound of the invention in a comparable dose was still active 18 hours after administration.

The acute toxicity in mice of GF 74 shows a LD$_{50}$ of 845 mg/kg by subcutaneous injection, and of 500 mg/kg by oral administration.

The compound shows about 10 times greater activity in 5HT-tests than in NA-tests.

Thus, GF 74 is active as an antidepressant in daily doses of 15–25 mg. In comparison, daily doses of 200–300 mg of imipramine are recommended.

We claim:

1. A 3-substituted 1-alkyl-4-fluorophenyl-piperidine of the formula

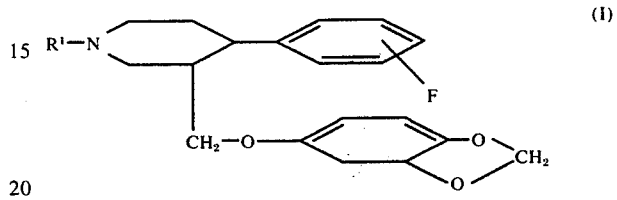

wherein R$^1$ represents hydrogen or an alkyl group of 1–4 carbon atoms;
the fluorine atom may be in any of the available positions; and a salt thereof with a pharmaceutically acceptable acid.

2. A compound according to claim 1, in which R$^1$ is hydrogen.

3. A compound according to claim 1, in which R$^1$ is methyl.

4. A compound according to claim 1, in which the fluorine is in para position.

* * * * *

UNITED STATES PATENT AND TRADEMARK OFFICE
CERTIFICATE OF CORRECTION

PATENT NO. : 4,007,196
DATED : Feb. 8, 1977
INVENTOR(S) : Jørgen Anders Christensen and Richard Felt Squires It is certified that error appears in the above-identified patent and that said Letters Patent are hereby corrected as shown below:

Column 5, the heading under Example 1 should read as follows:

-- (-)-α-4-(4-fluorophenyl)-3-(1,3-benzdioxolyl-(3)-oxymethyl)-N-methyl-piperidine,hydrochloride--;

Column 5, line 64, delete "methyl-" at the end of the line;

Column 6, lines 43-45 should read as follows:

--yielding 15.8 g of (-)-α-4-(4-fluorophenyl)-3-(1,3-benzdioxolyl-(3)-oxymethyl)-N-methyl-piperidine, hydrochloride--.

Column 6, line 15, "fluorophenyl)-3-hydroxymethylpiperidine" should read

-- fluorophenyl)-3-hydroxymethyl-N-methyl-piperidine --.

Signed and Sealed this

Twenty-fourth Day of March 1981

[SEAL]

Attest:

RENE D. TEGTMEYER

Attesting Officer

Acting Commissioner of Patents and Trademarks

UNITED STATES PATENT AND TRADEMARK OFFICE
CERTIFICATE OF CORRECTION

PATENT NO. : 4,007,196  
DATED : February 8, 1977  
INVENTOR(S) : Jørgen A. Christensen and Richard F. Squires It is certified that error appears in the above—identified patent and that said Letters Patent is hereby corrected as shown below:

On the title page:

Item [57], the ABSTRACT, line 1, delete "1-alkyl-";

Column 1, lines 7, 11 and 18, delete "1-alkyl-";

rewrite the formula bridging lines 20 and 25 as follows:

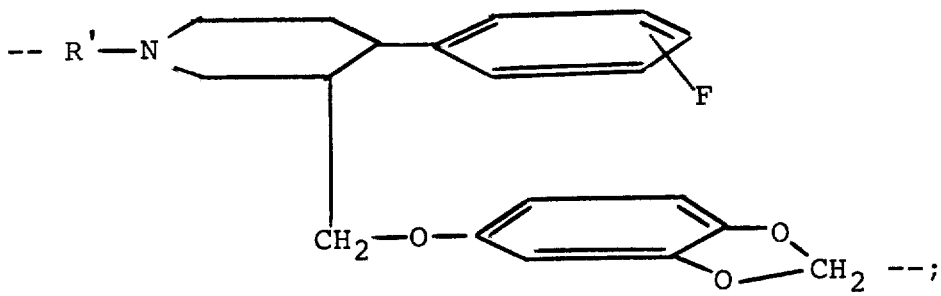

Column 2, line 17, change "resulved" to -- resolved --;
  line 66, change "sulfo-" to -- sulfonyl- --;
Column 3, line 58, after "invention" insert -- wherein $R^1$ is alkyl --;
Columns 3 and 4, in the middle of the page, below "M = menthol group", delete "+β";

UNITED STATES PATENT AND TRADEMARK OFFICE
CERTIFICATE OF CORRECTION

PATENT NO. : 4,007,196

DATED : February 8, 1977

INVENTOR(S) : Jørgen A. Christensen and Richard F. Squires

It is certified that error appears in the above—identified patent and that said Letters Patent is hereby corrected as shown below:

Column 4, line 3, change "racemic form" to -- mixture of diastereoisomers --;
        line 65, delete "menthol esters of";
        line 68, change "1,3-benzdioxolyl chloride" to -- 1,3-benzodioxol-5-ol --;

Column 5, line 50, change "-(3))-" to -- -(5))- --;
        line 51, change "oxymethyl-N-methyl-piperidine maleate" to -- oxymethyl-1-methyl-piperidine hydrochloride --;
        line 52, change "N-methyl-" to -- 1-methyl --;
        line 64, delete "methyl-";

Column 6, line 15, change "flurophenyl)-3-hydroxymethyl-piperidine." to -- fluorophenyl)-3-hydroxymethyl-1-methyl-piperidine --;
        line 48 (the heading of EXAMPLE 2), change "-(3))-" to -- -(5))- --;
        line 68, change "-(3))-" to -- -(5))- --;

Column 7, line 8 (the heading of EXAMPLE 3), after "racemic" insert -- α --;
        line 9, change "-(3))-" to -- -(5))- --;
        line 18 (the heading of EXAMPLE 4), change "-(3)-" to -- -(5)- --;
        line 56, (in EXAMPLE 4 D.), change "-(3)-" to -- -(5)- --;

UNITED STATES PATENT AND TRADEMARK OFFICE
CERTIFICATE OF CORRECTION

PATENT NO. : 4,007,196
DATED : February 8, 1977
INVENTOR(S) : Jørgen A. Christensen and Richard F. Squires It is certified that error appears in the above—identified patent and that said Letters Patent is hereby corrected as shown below:

Column 8, line 2, change "β" to -- α --;
    line 3, change "-(3)-" to -- -(5)- --;

Column 9, Claim 1, line 1, delete "1-alkyl-";

Column 10, Claim 1, rewrite the formula bridging lines 15 and 20 as follows:

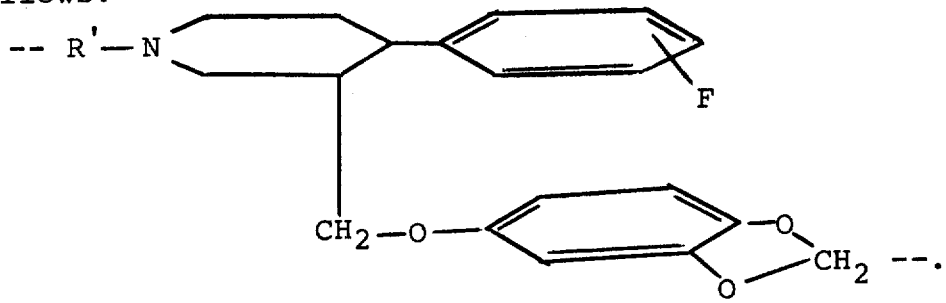

Signed and Sealed this

Eighth Day of March 1983

[SEAL]

Attest:

GERALD J. MOSSINGHOFF

Attesting Officer    Commissioner of Patents and Trademarks